US008256263B2

(12) United States Patent
Melsheimer (10) Patent No.: US 8,256,263 B2
(45) Date of Patent: Sep. 4, 2012

(54) APPARATUS AND METHOD FOR COMPRESSING A STENT

(75) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 925 days.

(21) Appl. No.: 12/261,747

(22) Filed: Oct. 30, 2008

(65) Prior Publication Data

US 2009/0113693 A1    May 7, 2009

Related U.S. Application Data

(60) Provisional application No. 60/985,449, filed on Nov. 5, 2007.

(51) Int. Cl.
*B21D 41/04* (2006.01)
*B21D 39/04* (2006.01)
*B23Q 3/00* (2006.01)

(52) U.S. Cl. ............... 72/402; 29/283.5; 29/282

(58) Field of Classification Search ............ 72/402; 29/283.5, 516, 515, 282; 623/1.11, 1.12, 623/1.15, 1.18

See application file for complete search history.

(56) References Cited

U.S. PATENT DOCUMENTS

| 1,051,777 | A | 1/1913 | St. Mars |
| 5,437,083 | A | 8/1995 | Williams et al. |
| 6,092,273 | A | 7/2000 | Villareal |
| 6,125,523 | A | 10/2000 | Brown et al. |
| 6,202,272 | B1 | 3/2001 | Jackson |
| 6,352,547 | B1 | 3/2002 | Brown et al. |
| 6,387,117 | B1 | 5/2002 | Arnold, Jr. et al. |
| 6,726,713 | B2 | 4/2004 | Schaldach et al. |
| 7,316,148 | B2 * | 1/2008 | Asmus et al. .......... 72/402 |
| 7,963,142 | B2 * | 6/2011 | Goff ...................... 72/402 |
| 2006/0171982 | A1 | 8/2006 | Timm |

* cited by examiner

*Primary Examiner* — Dana Ross
*Assistant Examiner* — Mohammad I Yusuf (57) ABSTRACT

An apparatus for compressing a stent includes a flexible sheet having a first portion curved over toward a second portion of the sheet, such that the sheet includes a generally cylindrical opening. A compression wedge and a curved surface of a platen sandwich at least the second portion of the sheet, and the compression wedge is adjacent to the generally cylindrical opening. A size of the generally cylindrical opening is changed by relative curvilinear motion of the compression wedge and the platen.

22 Claims, 5 Drawing Sheets

Fig.1A  Fig.1B

PRIOR ART

APPARATUS AND METHOD FOR COMPRESSING A STENT

RELATED APPLICATION

The present patent document claims the benefit of the filing date under 35 U.S.C. §119(e) of U.S. Provisional Patent Application Ser. No. 60/985,449, which was filed on Nov. 5, 2007, and is hereby incorporated by reference in its entirety.

TECHNICAL FIELD

The present disclosure is related generally to a compression apparatus, and more particularly to a method and apparatus for compressing a stent.

BACKGROUND

Stents are generally designed as tubular support structures that can be used in a variety of medical procedures to treat blockages, occlusions, narrowing ailments and other problems that restrict flow through body vessels. Typically, a stent is radially compressed to a reduced diameter for transport within a vessel and then radially expanded to contact the vessel wall once in place at a treatment site. Radial compression of the stent is typically carried out in a compression apparatus.

Figure 1A:
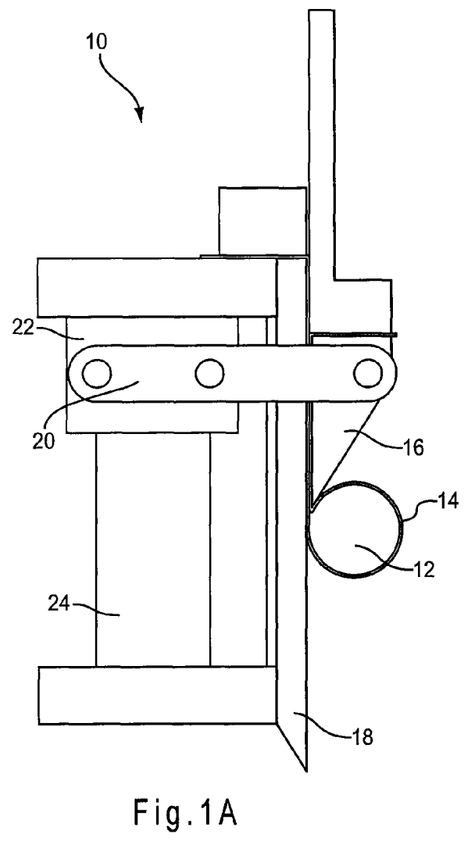
FIGS. 1A and 1B are schematics of a prior art apparatus for compressing a stent.
Figure 1B:
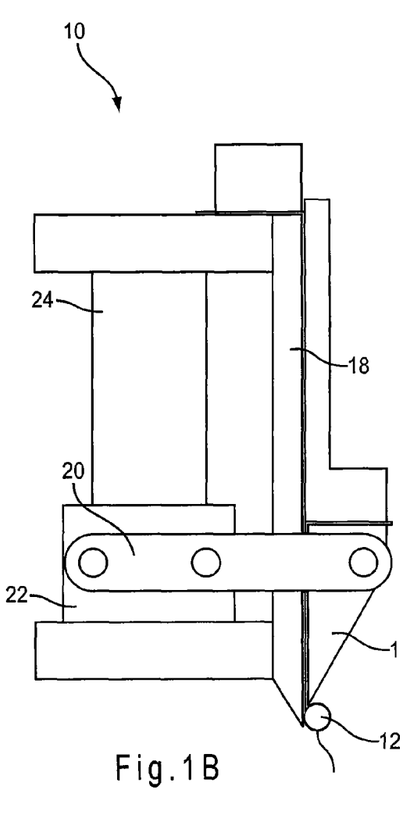

FIGS. 1A and 1B are schematics of a prior art apparatus 10 for radially compressing a stent to a reduced diameter configuration. Referring to FIG. 1A, a cylindrical opening 12 is formed in a sheet 14 sandwiched between a wedge 16 and a support 18. The apparatus 10 employs linear motion of the wedge 16 to alter the diameter of the cylindrical opening 12. By moving the wedge 16 across the support 18 toward or away from the cylindrical opening 12, the size of the opening 12 can be reduced or expanded, as shown schematically in FIG. 1B. Accordingly, a stent placed in the cylindrical opening 12 may be radially compressed as the wedge 16 moves across the support 12 and decreases the size of the opening 12. The support 18 remains stationary as the wedge 16 moves.

To facilitate motion of the wedge 16, a first control arm 20 is connected to the wedge 16 at one end and to a linear bearing 22 at the other end. A second control arm (not visible in figure) is disposed behind the first control arm 22 and connected to a second linear bearing (also not visible). Each linear bearing 22 is disposed about a cylindrical shaft 24 positioned perpendicular to the cylindrical opening 12. When the linear bearings 22 are moved along their respective shafts 24, the control arms 20 drive the wedge 16 across the support 18, thereby changing the size of the cylindrical opening 12.

It is important to be able to control the gap or spacing between the wedge 16 and the support 18. Any misalignments of the linear bearings 22 with respect to the support 18 or each other may cause the spacing to vary as the bearings 22 travel along their respective cylindrical shafts 24. If the gap is too large, a stent placed in the cylindrical opening 12 may be squeezed between the opposing portions of the sheet 14 during the compression. If the gap is too small, frictional forces may increase. It is desirable to use small, lightweight linear bearings to minimize bearing friction and permit high resolution feedback of the compression forces being applied to the stent; however, such linear bearings 22 tend to flex during the compression of larger stents, allowing the size of the gap between the wedge 16 and the support 18 to increase. Consequently, larger, stiffer linear bearings 22 are generally employed, and the distance between the support 18 and the bearings 22 is minimized. The forces needed to move the massive bearings 22 can be so large, however, that the operator's ability to monitor compression forces at the desired resolution may be impaired. Also, at short distances between the bearings 22 and the support 18, the stent can be exposed to contamination from the bearing surfaces, and it may be problematic to carry out the compression in a controlled atmosphere and/or at tightly controlled or extreme temperatures.

Due to the shortcomings of the prior art apparatus described above, it would be advantageous to develop an improved apparatus and method for compressing a stent.

BRIEF SUMMARY

Described herein are a new apparatus and method for radially compressing an expandable stent that provides advantages over existing devices and methods. The new compression apparatus is believed to be less susceptible to alignment problems than a prior art device since the relationships among the components may be more tightly controlled and fine-tuned. Also, lower forces may be utilized to move the compression apparatus, and the compressive forces being applied to the stent may be detected with greater sensitivity. In addition, bearing surfaces are kept remote from the compression region, thereby minimizing contamination issues and facilitating the use of tightly controlled or extreme (e.g., cryogenic) temperatures and/or a controlled atmosphere for compression.

According to one embodiment, the new apparatus includes a flexible sheet having a first portion curved over toward a second portion of the sheet, such that the sheet includes a generally cylindrical opening. A compression wedge and a curved surface of a platen sandwich at least the second portion of the sheet, and the compression wedge is adjacent to the generally cylindrical opening. A size of the generally cylindrical opening is changed by relative curvilinear motion of the compression wedge and the platen.

According to another embodiment, the new apparatus includes a flexible sheet disposed on a platen having a curved surface, where a first portion of the sheet is curved over toward a second portion of the sheet such that the sheet includes a generally cylindrical opening. The apparatus further includes at least one control arm comprising a pivot point. The pivot point is spaced apart from the generally cylindrical opening a distance corresponding to a radius of curvature of the curved surface of the platen. A size of the generally cylindrical opening is changed by pivotal motion of the control arm about the pivot point.

A method of compressing an expandable stent includes providing a flexible sheet disposed on a platen having a curved surface, where a first portion of the sheet is curved over toward a second portion of the sheet such that the sheet includes a generally cylindrical opening. Also provided is at least one control arm comprising a pivot point spaced apart from the generally cylindrical opening by a distance corresponding to a radius of curvature of the curved surface of the platen. The method further includes positioning a stent within the generally cylindrical opening and moving the control arm about the pivot point, thereby reducing the size of the generally cylindrical opening and radially compressing the stent.

DETAILED DESCRIPTION

Figure 2A:
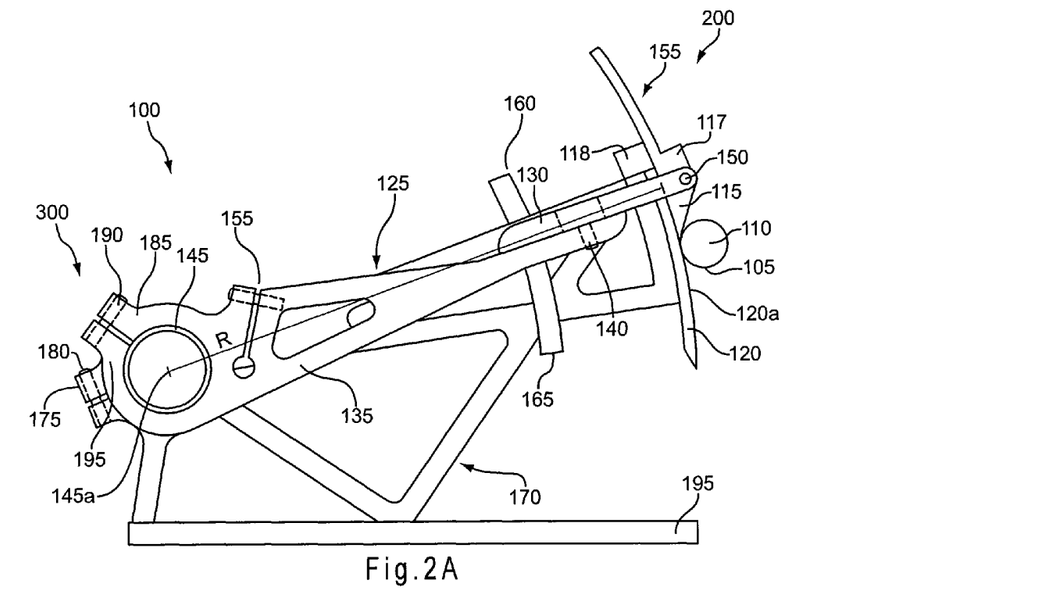
FIGS. 2A and 2B are schematics of a new apparatus for compressing a stent, according to a first embodiment of the apparatus.
Figure 2B:
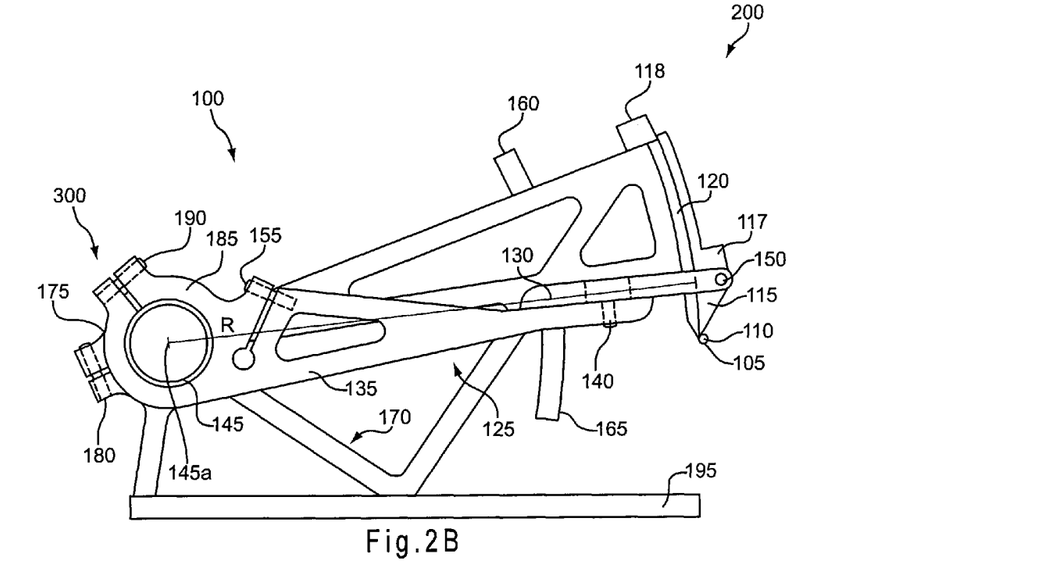

FIGS. 2A and 2B show the new compression apparatus 100 according to a first embodiment. The apparatus includes a compression region 200 and a remote pivot region 300 linked by at least one control arm 125.

Figure 3A:
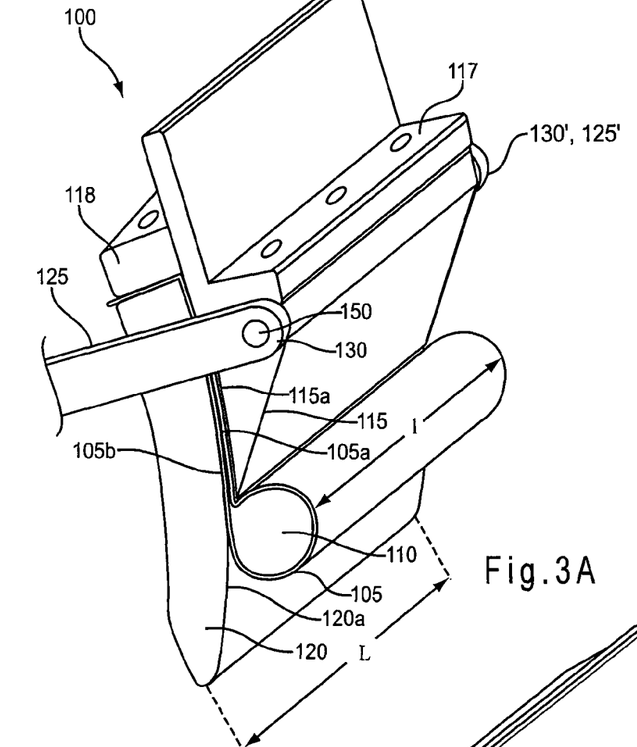
FIGS. 3A and 3B are schematics of the compression region of the new apparatus, according to one embodiment of the compression region.
Figure 3B:
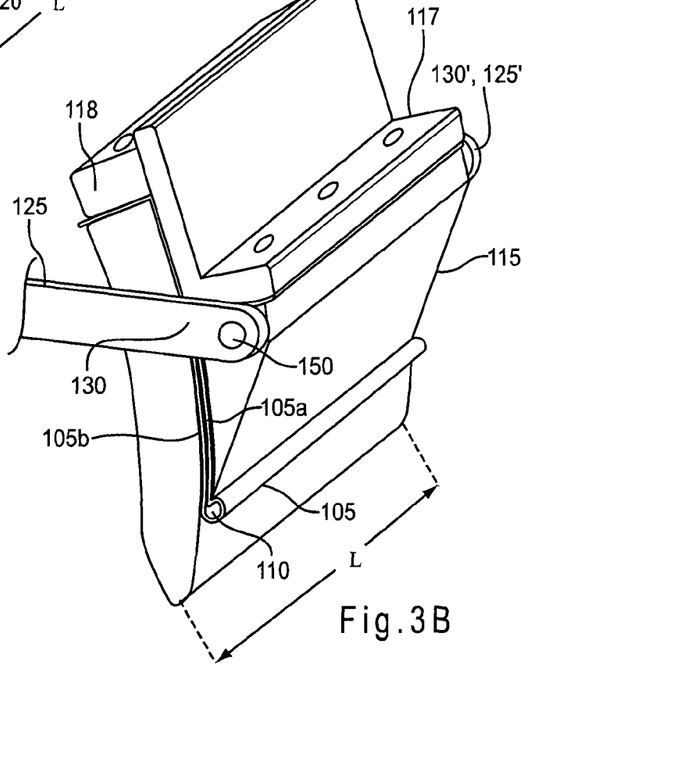

FIGS. 3A and 3B show the compression region 200 of the apparatus 100 according to one embodiment. The compression region 200 includes a flexible sheet 105 having a first portion 105a curved over toward an opposing second portion 105b of the sheet 105. The flexible sheet 105 thereby includes a generally cylindrical opening 110. The cylindrical opening 110 has a size sufficient to accommodate a stent, as will be discussed further below. The second portion 105b of the sheet 105 is disposed between (i.e., sandwiched by) a compression wedge 115 and a curved surface 120a of a platen 120. The first portion 105a of the sheet 105 may also be disposed between the compression wedge 115 and the platen 120, as shown in FIG. 3A. The platen 120 may be described as supporting or underlying the first and second portions 105a, 105b of the sheet 105. The compression wedge 115 is positioned adjacent to the generally cylindrical opening 110 and may be described as being on or overlying the second portion 105b of the sheet 105. The compression wedge 115 may also be on or overlying the first portion 105a of the sheet 105.

The size (e.g., diameter) of the generally cylindrical opening 110 may be changed by relative motion of the compression wedge 115 and the platen 120. Accordingly, the diameter of a stent disposed within the generally cylindrical opening 110 may be controllably reduced or expanded by the relative motion of the compression wedge 115 and the platen 120.

As shown in FIGS. 3A and 3B, the compression wedge 115 may move across the sheet 105 and the platen 120 to change the size of the generally cylindrical opening 110. When the motion of the compression wedge 115 is in a direction toward the generally cylindrical opening 110, the size of the opening 110 decreases. When the motion of the compression wedge 115 is in a direction away from the generally cylindrical opening 110, the size of the opening 110 increases. Preferably, the apparatus 100 is employed to crimp or compress a stent by moving the compression wedge 115 in the direction of the generally cylindrical opening 110. According to this embodiment, the platen 120 remains stationary during the compression operation.

According to an alternative embodiment, the compression wedge 115 may remain stationary and the platen 120 may be moved to produce the relative motion, thereby reducing or expanding the size of the generally cylindrical opening 110 of the sheet 105, as will be discussed further below. In yet another embodiment, both the compression wedge 115 and the platen 120 may be moved simultaneously to produce the relative motion.

Figure 4:
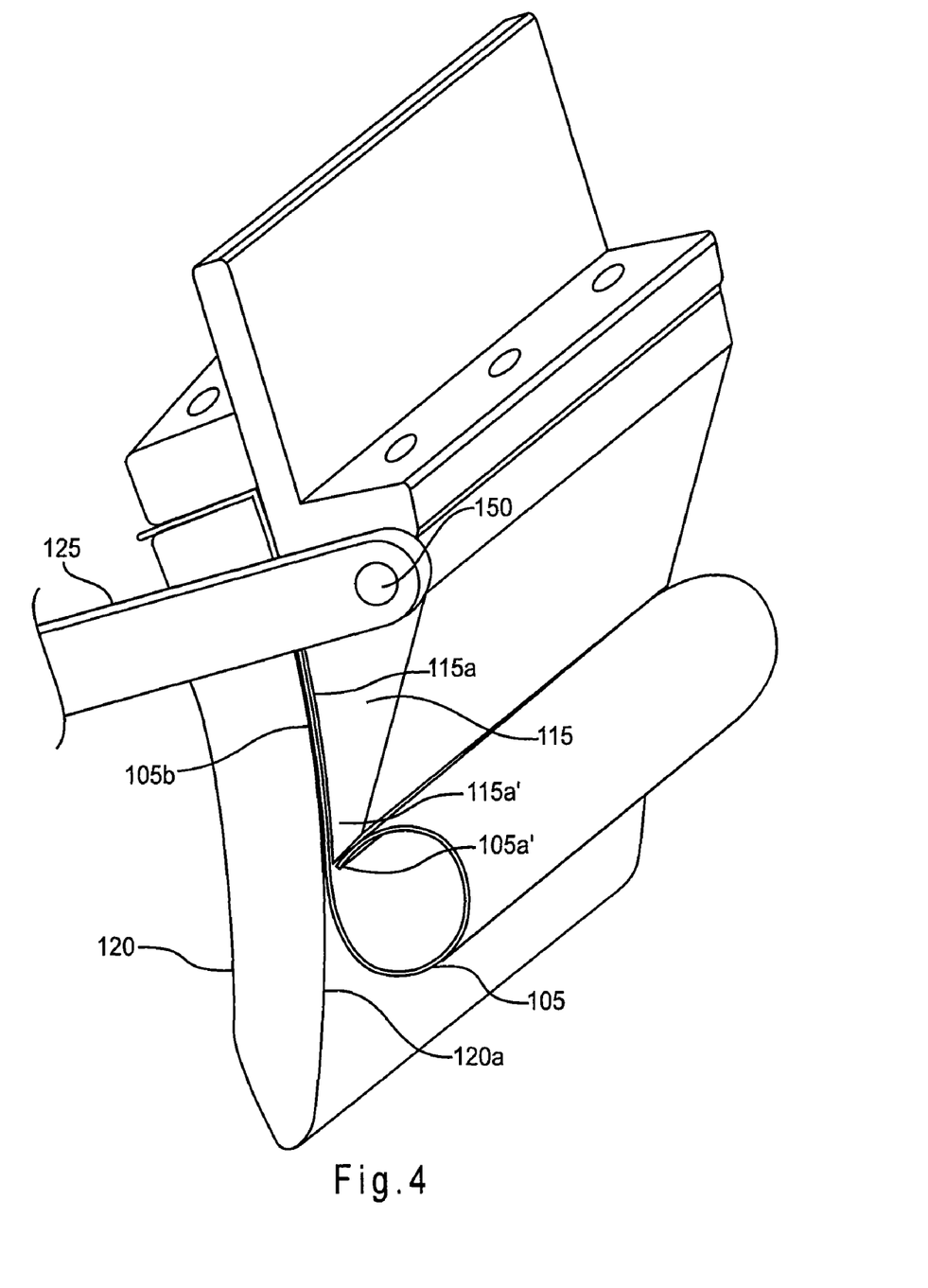
FIG. 4 is a schematic of the compression region of the new apparatus, according to another embodiment of the compression region.

Preferably, the second portion 105b of the sheet 105 is secured to the platen 120. It is also preferred that the first portion 105a of the sheet 105 is secured to the compression wedge 115. One approach to securing the second portion 105b of the sheet 105 to the platen 120 is shown in FIG. 3A. According to this embodiment, the second portion 105b may extend alongside the platen 120 in a direction away from the generally cylindrical opening 110 and be fastened between the platen 120 and a second clamp 118 disposed behind the platen 120. A similar approach may be employed with the first portion 105a of the sheet 105. The first portion 105a may extend alongside the compression wedge 115 in a direction away from the generally cylindrical opening 110 and be secured between the compression wedge 115 and a first clamp 117 disposed behind the compression wedge 115. Alternatively, the first portion 105a of the sheet 105 may not extend alongside the compression wedge 115 in a direction away from the generally cylindrical opening 110. Instead, for example, a leading edge 105a' of the sheet 105 may be secured to a leading edge 115a' of the compression wedge 115, as shown in FIG. 4. According to this embodiment, only the second portion 105b of the sheet 105 is sandwiched between the compression wedge 115 and the platen 120.

Due to the curved surface of the platen 120, the relative motion between the compression wedge 115 and the platen 120 occurs over a curvilinear path. The curved surface 120a of the platen 120 preferably has a convex curvature. It is also preferred that the curved surface 120a of the platen 120 is a portion of a cylindrical surface having a longitudinal dimension L and a radius of curvature R. Preferably, the radius of curvature R is much greater than the diameter of the stent. A large radius of curvature R may allow the compression operation to occur a substantial distance away from bearing surfaces that may contain contaminants detrimental to the stent and/or the compression operation. A large radius of curvature R may also help to minimize the forces needed to move the components of the compression apparatus 100. Preferably, the radius of curvature R is between about 5 cm and about 50 cm. The radius of curvature may also be between about 10 cm and about 50 cm, or between about 10 cm and about 25 cm. In some situations, such as potential bedside use of the apparatus, a smaller radius of curvature may be desirable (e.g., between about 5 cm and about 20 cm). A larger radius of curvature may be advantageous in other situations, such as where a controlled atmosphere is used for the compression or if contamination is a particular concern. In these cases, the desired radius of curvature may be, for example, between about 30 cm and 50 cm. According to one embodiment, the radius of curvature R is about 15 cm.

Preferably, the longitudinal dimension L of the curved surface 120a of the platen 120 is at least as large as a length of a stent. For example, the longitudinal dimension L may lie in the range of from about 30 mm to about 150 mm, according to one embodiment. The longitudinal dimension L may also be long enough to accommodate more than one stent. For example, two or more stents may be disposed end to end within the cylindrical opening 110. Accordingly, the longitudinal dimension L of the portion of the cylindrical surface may be much longer than 150 mm. For example, the longitudinal dimension L may lie in the range of from about 30 mm to about 1,000 mm (1 m), according to one embodiment.

A length l of the cylindrical opening 110 formed in the sheet 105 may also be at least as large as a length of a stent. For example, the length l may lie in the range of from about 30 mm to about 150 mm, according to one embodiment. The length l may also be long enough to accommodate more than one stent, as described above. Accordingly, the length l may be much longer than 150 mm. For example, the length l may lie in the range of from about 30 mm to about 1,000 mm (1 m), according to one embodiment.

The flexible sheet 105 may be formed of a metal or polymer such as stainless steel or polyimide (e.g., Kapton). The sheet

105 preferably has a thickness in the range of from about 0.0127 mm (0.0005 inch) to about 0.0762 mm (0.0030 inch). For example, a stainless steel sheet of about 0.0381 mm (0.0015 inch) may be suitable. Alternatively, a Kapton sheet of about 0.0508 mm (0.0020 inch) may be used as the flexible sheet 105. Generally, such a sheet 105 is supplied in the form of a roll. When unrolled, the sheet 105 may advantageously conform to the curved surface 120a of the platen 120 more stably and predictably than to a flat surface.

The compression wedge 115 is shown having a wedge shape in FIGS. 3A and 3B; however, other configurations of the compression wedge 115 are possible. For example, the compression wedge may have a blade-like shape in which there is essentially only a line of contact (as opposed to a surface of contact) between the compression wedge and the flexible sheet. Alternatively, the compression wedge may have a block-like or other shape in which there is a surface of contact between the wedge and the sheet. Preferably, when there is a surface of contact, as shown in FIGS. 3A and 3B, the surface 115a of the compression wedge 115 facing the platen 120 has a curvature determined by the curved surface 120a of the platen 120. For example, the surface 115a of the compression wedge 115 may be concave, while the curved surface 120a of the platen 120 is preferably convex. Accordingly, the two surfaces 115a, 120a may substantially fit together as mating surfaces. The compression wedge 115 may be machined out of stainless steel or another biocompatible material, such as, for example, a polyamide (e.g., nylon), a polyimide (e.g., Kapton), polytetrafluoroethylene (PTFE), polyethylene (e.g., ultra-high molecular weight polyethylene (UHMWPE)), polyetheretherketone (PEEK), polyacetal (e.g., Delrin), or polyurethane (e.g., Isoplast).

The gap or spacing between the compression wedge 115 and the platen 120 may be controlled to lie within a predetermined range. If the spacing is too large, the stent may be squeezed or lodged between the compression wedge 115 and the platen 120 during the compression operation. If the spacing is too small, on the other hand, the relative motion of the compression wedge 115 and the platen 120 may be impaired by frictional forces between opposing portions of the sheet 105 and possibly by particulate generation. The preferred gap or spacing depends in part on the thickness of the flexible sheet 115, which was discussed above. Accordingly, the gap or spacing may be maintained within the range of from about 0.01 mm to about 0.2 mm. The apparatus 100 includes fine-tuning adjustments for controlling the gap or spacing between the wedge 115 and the platen 120, and also for controlling the orientation of the wedge 115 with respect to the platen 120, as will be described further below.

At least one control arm may be employed to control the relative motion between the platen 120 and the compression wedge 115. Referring to the embodiment of FIGS. 2A and 2B, two control arms 125, 125' may link the compression region 200 of the apparatus 100 to the remote pivot region 300. (A portion of the second control arm 125' is visible in FIG. 3A.) In particular, a secured end of each control arm 125, 125' is preferably connected to a cylindrical pivot shaft 145 disposed away from the cylindrical opening 110. A working end of each control arm 125, 125' is in communication with, according to this embodiment, the compression wedge 115. As the control arms 125, 125' pivot about the radial center 145a of the cylindrical shaft 145, the compression wedge 115 moves in a curvilinear trajectory over the platen 120, which is stationary according to the embodiment of FIGS. 2A and 2B. Because the motion of the control arms 125, 125' occurs about a common pivot point (the radial center 145a), the alignment challenges of the prior art apparatus 10 (see FIG. 1A) may be reduced. The control arms 125, 125' may move with the cylindrical shaft 145 or rotate about the cylindrical shaft 145, as discussed further below.

Preferably, the cylindrical shaft 145 is disposed parallel to the cylindrical opening 110. It is also preferred that the radial center 145a of the cylindrical shaft 145 is spaced apart from the cylindrical opening 110 a distance defined by the radius of curvature R of the curved surface 120a of the platen 120. Similarly, each control arm 125, 125' has a length defined by the radius of curvature R of the curved surface 120a of the platen 120. According to one embodiment, the control arms 125, 125' are at least as long as the radius of curvature R. The radius of curvature R may range from about 10 cm to about 50 cm, according to one embodiment. Accordingly, the length of the control arms 125, 125' may range from about 10 cm to about 50 cm.

Each control arm 125, 125' may include more than one piece or segment. For example, the control arm 125 shown in FIG. 2A includes a first segment 130 fastened to a second segment 135 by a fastener 140. According to this embodiment, the first segment 130 of the control arm 125 is connected to the compression wedge 115, and the second segment 135 of the control arm 125 is connected to the cylindrical shaft 145 disposed away from the cylindrical opening 110. By adjusting the relative positioning of the first segment 130 and the second segment 135 (e.g., via a slot) and tightening down on the fastener 140 connecting the two, it may be possible to make fine adjustments to the gap or spacing between the compression wedge 115 and the platen 120. A pinch bolt 155 located near the pivot region 300 may allow for tuning the position of one control arm 125 with respect to the other control arm 125', thus ensuring that the generally cylindrical opening 110 is properly oriented with respect to the cylindrical shaft 145. It may also be advantageous for the first segment 130 of the control arm 125 (or the working end of a control arm including just a single segment) to be pivotally connected to the compression wedge 115 at the pivot axle 150. A torsion spring may be mounted on the pivot axle 150 to provide control over the pressure exerted by the compression wedge 115 on the sheet 105 as it traverses the platen 120 (or as the platen 120 moves relative to the compression wedge 115).

A frame 170 may support the platen 120, as shown in FIGS. 2A and 2B. The frame 170 may also be in communication with the cylindrical shaft 145. For example, the frame 170 may be attached to the cylindrical shaft 145 by a clamp 175 which is secured by a pinch bolt 180. The clamp 175 may house bushings or bearings to permit the cylindrical shaft 145 to rotate therein with minimal frictional forces. For example, Teflon bushings, ball bearings, or roller bearings may be employed. The second segment 135 of the control arm 125 may also include a clamp 185 disposed about the cylindrical shaft 145 and secured by a pinch bolt 190. This clamp 185 is preferably tightly secured to the cylindrical shaft 145 so that the control arms 125, 125' rotate along with the shaft 145. Alternatively, the cylindrical shaft 145 could remain stationary and be tightly secured to the frame 170 by the clamp 175, while each control arm 125, 125' rotates about the shaft 145. In this case, the clamp 185 could house bearings or bushings to facilitate carrying out the pivotal motion with minimal friction.

The pivotal motion of the control arms 125, 125', and thus the curvilinear motion of the component connected thereto (the wedge 115, according to the embodiment of FIG. 2A, or the platen 120, as will be discussed below), may be initiated manually or automatically. For example, the compression wedge 115 may be moved along its curvilinear trajectory by manually applying force to the clamp 117 behind the wedge 115. Alternatively, the apparatus 100 may include an actuator in communication with the control arm 125 to effect the curvilinear motion. According to one embodiment, the actuator may be a pneumatic actuation cylinder or an electric actuator. The actuator may be secured, for example, to a stationary upper bracket 160 attached to the frame 170 supporting the platen 120 and to a lower bracket 165 attached to the control arm 125. The actuator is preferably mounted as close to the platen 120 as possible without interfering with the compression operation. The farther away from the cylindrical shaft 145 the force is applied to the control arm 125, the lower the amount of force needed to induce the pivotal motion of the arm 125.

Preferably, a counterweight is used to balance the apparatus 100 and prevent unwanted motion of the control arms 125, 125' due to gravitation forces. In a counterbalanced configuration, the apparatus may have an increased sensitivity for the detection of compression forces. According to an embodiment in which the control arms 125, 125' move with the cylindrical shaft 145, the shaft 145 may be wrapped with a cable attached to a specified mass to achieve a counterbalanced configuration of the apparatus 100. Alternatively, it is envisioned that the apparatus could be adapted for use such that the control arm pivots in a horizontal plane with respect to the ground; thus, the effects of gravity on the motion thereof could be avoided without use of a counterweight.

Figure 5A:
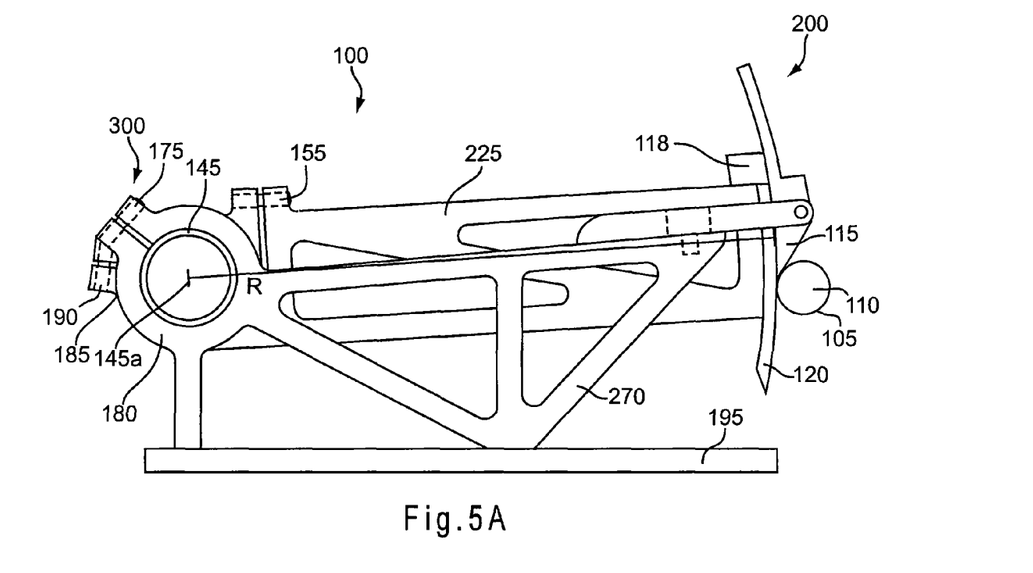
FIGS. 5A and 5B are schematics of the new apparatus for compressing a stent, according to a second embodiment of the apparatus.
Figure 5B:
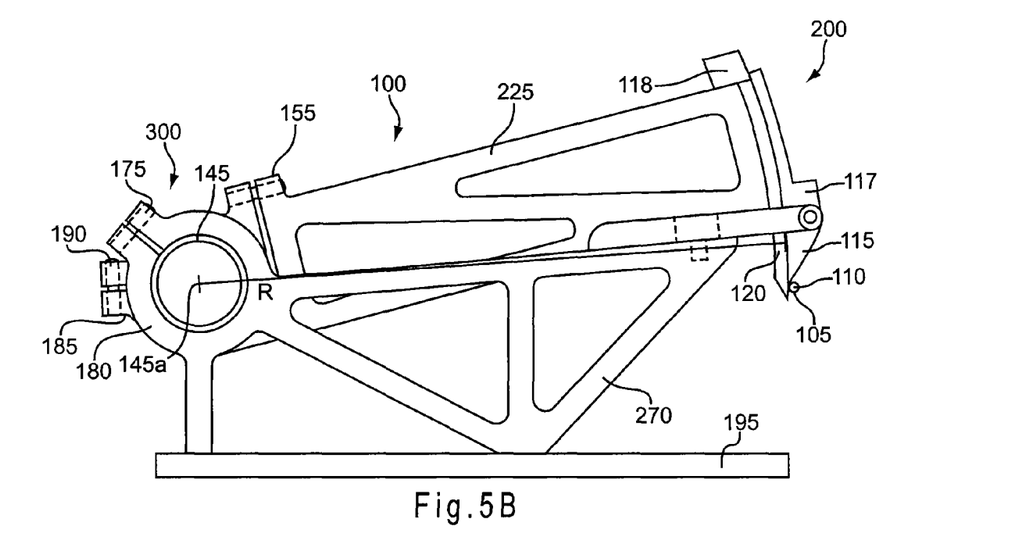

FIGS. 5A and 5B show a second embodiment of the apparatus 100 in which the relative motion of the compression wedge 115 and the platen 120 may be achieved by curvilinear motion of the platen 120 while the compression wedge 115 remains stationary. According to this embodiment, the working end of the control arm 225 may be connected to the platen 120 and the secured end is connected to a cylindrical shaft 145 disposed away from the cylindrical opening 110. The configuration of the flexible sheet 105 and the cylindrical opening 110 may be the same as in the previous embodiment. The second portion 105b of the sheet 105 may be secured to the platen 120, and the first portion of the sheet 105 may be secured to the compression wedge 115. Motion of the control arm 225 may be initated manually or by an actuator, as in the previous embodiment. As the control arm 225 pivots about the radial center 145a of the cylindrical shaft 145, the platen 120 moves in a curvilinear trajectory with respect to the compression wedge 115, thereby causing a change in the diameter of the generally cylindrical opening 110. According to this embodiment, the compression wedge 115 may be supported and held in place by a frame 270 attached to a support 195. The frame 270 may include more than one piece or segment, similar to the control arm 125 of the previous embodiment, to facilitate fine-tuning adjustments of the spacing between the compression wedge 115 and the platen 120, as described above. The cylindrical shaft 145 is preferably disposed parallel to the generally cylindrical opening 110, and each of the one or more control arms 225 has a length defined by the radius of curvature R of the curved surface of the platen 120, as in the previous embodiment.

Also described herein is a method for compressing an expandable stent. The method entails providing a flexible sheet having a first portion curved over toward an opposing second portion of the sheet such that the sheet includes a generally cylindrical opening. The first and second portions of the sheet are preferably sandwiched between the curved surface of a platen and a compression wedge. The compression wedge is disposed adjacent to the cylindrical opening. The method further entails positioning a stent within the generally cylindrical opening, and moving at least one of the compression wedge and the platen along a curvilinear trajectory to reduce the size of the cylindrical opening. The stent is thereby radially compressed within the opening. In carrying out the method, the compression wedge may move while the platen remains stationary. Alternatively, the platen may move while the compression wedge remains stationary. It is also envisioned that the platen and the compression wedge may both move relative to one another along the curvilinear trajectory to reduce the size of the cylindrical opening.

According to another aspect, the method entails providing a flexible sheet disposed on a platen having a curved surface. A first portion of the sheet is curved over toward an opposing second portion of the sheet such that the sheet includes a generally cylindrical opening. A control arm having a pivot point spaced apart from the generally cylindrical opening a distance corresponding to a radius of curvature of the curved surface of the platen is also provided.

To carry out the compression, a stent is positioned within the generally cylindrical opening, and the control arm moves about the pivot point, thereby reducing the size of the generally cylindrical opening. The stent is thus radially compressed within the opening. Preferably, moving the control arm about the pivot point induces relative curvilinear motion of the platen and a compression wedge, which is disposed on the flexible sheet adjacent to the generally cylindrical opening.

The pivot point may be a radial center of a cylindrical shaft oriented parallel to the generally cylindrical opening and connected to one end of the control arm. The other end of the control arm may be connected with the platen having the curved surface, according to one embodiment. Accordingly, the pivotal motion of the control arm results in curvilinear motion of the platen, which reduces the size of the opening and compresses the stent. Alternatively, the other end of the control arm may be connected to a compression wedge disposed on the flexible sheet adjacent to the cylindrical opening. In this case, the pivotal motion of the control arm results in curvilinear motion of the compression wedge, which reduces the size of the opening and compresses the stent.

A new apparatus and method for compressing a stent have been described herein. The new apparatus may be less susceptible to alignment problems than existing devices since the relationships among the components may be tightly controlled and fine-tuned. It is also believed that lower forces are needed to move the new apparatus; thus, compressive forces being applied to the stent may be detected with greater sensitivity. In addition, bearing surfaces are kept remote from the compression region, thereby minimizing contamination issues and facilitating the use of extreme or tightly controlled temperatures and/or a controlled environment for compression.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. An apparatus for radially compressing an expandable stent, the apparatus comprising:

a flexible sheet having a first portion curved over toward a second portion of the sheet, the sheet thereby including a generally cylindrical opening;
a compression wedge and a curved surface of a platen sandwiching at least the second portion of the sheet, the second portion of the sheet being secured to the platen, and the compression wedge being adjacent to the generally cylindrical opening;
wherein a size of the generally cylindrical opening is changed by relative curvilinear motion of the compression wedge and the platen.

2. The apparatus of claim 1, wherein the compression wedge and the curved surface of the platen sandwich the first portion and the second portion of the sheet.

3. The apparatus of claim 1, wherein a spacing between the compression wedge and the curved surface of the platen is in the range of from about 0.01 mm to about 0.2 mm.

4. The apparatus of claim 1, wherein the first portion of the sheet is secured to the compression wedge.

5. The apparatus of claim 1, wherein the compression wedge has a concave surface facing the curved surface of the platen, the concave surface of the compression wedge and the curved surface of the platen substantially fitting together as mating surfaces.

6. The apparatus of claim 1, wherein the curved surface of the platen is a portion of a cylindrical surface, the curved surface thereby having a longitudinal dimension and a radius of curvature.

7. The apparatus of claim 6, wherein the longitudinal dimension is at least as large as a length of a stent.

8. The apparatus of claim 6, wherein the longitudinal dimension is in the range of from 30 mm to 150 mm.

9. The apparatus of claim 6, wherein the radius of curvature is at least about 5 cm.

10. The apparatus of claim 1, further comprising at least one control arm having a working end connected to one of the compression wedge and the platen and having a secured end connected to a cylindrical shaft disposed away from the cylindrical opening.

11. The apparatus of claim 10, wherein the cylindrical shaft is oriented parallel to the generally cylindrical opening.

12. The apparatus of claim 10, wherein the cylindrical shaft is disposed away from the generally cylindrical opening a distance corresponding to a radius of curvature of the curved surface of the platen.

13. The apparatus of claim 10, wherein the working end of the control arm is a separate segment from the secured end of the control arm, the working end being adjustably fastened to the secured end.

14. The apparatus of claim 10, wherein the working end of the control arm is connected to the compression wedge, and further comprising a frame for supporting the platen.

15. An apparatus for compressing an expandable stent, the apparatus comprising:
a flexible sheet disposed on a platen having a curved surface, a first portion of the sheet being curved over toward a second portion of the sheet, the sheet thereby including a generally cylindrical opening;
at least one control arm comprising a pivot point, the pivot point being spaced apart from the generally cylindrical opening by a distance corresponding to a radius of curvature of the curved surface of the platen;
wherein a size of the generally cylindrical opening is changed by pivotal motion of the control arm about the pivot point.

16. The apparatus according to claim 15, wherein the pivot point is a radial center of a cylindrical shaft oriented parallel to the generally cylindrical opening, a first end of the control arm being connected to the cylindrical shaft.

17. The apparatus according to claim 15, wherein a second end of the control arm is connected to the platen having the curved surface, the pivotal motion of the control arm causing curvilinear motion of the platen.

18. The apparatus according to claim 15, wherein a second end of the control arm is connected to a compression wedge disposed on the flexible sheet adjacent to the generally cylindrical opening, the pivotal motion of the control arm causing curvilinear motion of the compression wedge.

19. A method of compressing an expandable stent, the method comprising:
providing a flexible sheet disposed on a platen having a curved surface, a first portion of the sheet being curved over toward a second portion of the sheet, the sheet thereby including a generally cylindrical opening;
providing at least one control arm comprising a pivot point spaced apart from the generally cylindrical opening by a distance corresponding to a radius of curvature of the curved surface of the platen;
positioning a stent within the generally cylindrical opening;
moving the control arm about the pivot point, thereby reducing the size of the generally cylindrical opening and radially compressing the stent.

20. The method of claim 19, wherein moving the control arm about the pivot point induces relative curvilinear motion of the platen and a compression wedge, the compression wedge being disposed on the flexible sheet adjacent to the generally cylindrical opening.

21. The apparatus of claim 15, wherein the second portion of the flexible sheet is secured to the platen.

22. The method of claim 19, wherein the second portion of the flexible sheet is secured to the platen.

\* \* \* \* \*